United States Patent [19]
Smith

[11] 3,940,420
[45] Feb. 24, 1976

[54] COMPOUND, DITHIOBIS-(SUCCINIMIDYL PROPIONATE)

[75] Inventor: Paul K. Smith, Rockford, Ill.

[73] Assignee: Pierce Chemical Company, Rockford, Ill.

[22] Filed: July 15, 1974

[21] Appl. No.: 488,541

[52] U.S. Cl. .......................................... 260/326.26
[51] Int. Cl.² .................................... C07D 207/12
[58] Field of Search ............................. 260/326.26

[56] References Cited
OTHER PUBLICATIONS
Anderson et al., J.A.C.S., Vol. 86, pp. 1839–1842.

Primary Examiner—Stanley J. Friedman

[57] ABSTRACT

The present disclosure describes preparation of the novel compound, dithiobis-(succinimidyl propionate) represented by the following structure:

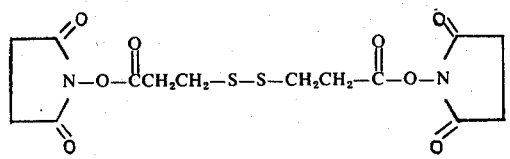

MW 404.42

1 Claim, No Drawings

COMPOUND, DITHIOBIS-(SUCCINIMIDYL PROPIONATE)

The present invention relates to new chemical compounds and, more particularly, to the novel compound, dithiobis-(succinimidyl propionate) which can be represented by the following structure:

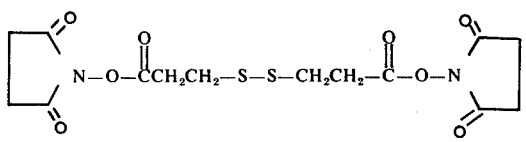

This new compound is useful for cross linking proteins (fixing) at mild conditions, and if desired, the fixing process can be reversed by cleaving the easily ruptured disulfide bond in the molecule. These applications are important in biochemical research (see Finn Wold, *Methods in Enzymology*, Vol. 25, p. 623) and in fields such as Electron Microscopy (see Hassell and Hand, *Journal of Histochemistry and Cytochemistry*, Vol. 22, No. 4, pp. 223–239).

The novel compound in this disclosure will react with free amino groups in natural or synthetic proteins to form stable peptide bonds. The use of N-hydroxysuccinimide esters is described (see Anderson et al. JACS 86, p. 1839–42 (1964)).

A typical preparation of dithiobis-(succinimidyl propionate) can be accomplished as follows: to a solution of dithiodipropionic acid (105.15 gm, .5 m) and N-hydroxysuccinimide (115.09 gm, 1.0 m) in 600 cc of Tetrahydrofuran at −5° C. was added dropwise a solution of 206.32 gm (1.0 m) of dicyclohexylcarbodiimide in 100 cc. of THF. The resulting reaction mixture was stirred at 0° C. for 24 hrs. After an additional 24 hrs. stirring at room temperature, the solid by-product, dicyclohexylurea, was filtered off and discarded. The filtrate was evaporated to dryness, taken up in ethyl acetate and the desired product precipitated by addition of hexane. The product after drying is a white (yield - 90 gm) powder M.P. 63°–5°. Further purification by recrystallization yields a product having a melting point of about 121°–123° C.

| Analysis for carbon: | Found | 41.45% | Theory | 41.58% |
|---|---|---|---|---|
| hydrogen | " | 4.13% | " | 3.99% |
| nitrogen | " | 6.78% | " | 6.93% |
| sulfur | " | 15.70% | " | 15.86% |

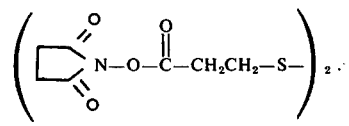

What is claimed is:
1. The compound dithiobis-(succinimidyl propionate) represented by the formula